United States Patent [19]

Riquier et al.

[11] Patent Number: 5,318,511

[45] Date of Patent: Jun. 7, 1994

[54] METHOD AND APPARATUS FOR CONTROLLING THE CIRCULATION OF BLOOD IN A SINGLE NEEDLE CIRCUIT

[75] Inventors: Jean-Claude Riquier, Rilleux; Jacques Chevallet, Serezin du Rhone, both of France

[73] Assignee: Hospal Industrie, France

[21] Appl. No.: 831,536

[22] Filed: Feb. 5, 1992

[30] Foreign Application Priority Data

Feb. 6, 1991 [FR] France .................... 91 01566

[51] Int. Cl.$^5$ .................................................. A61M 1/03
[52] U.S. Cl. ........................................ 604/4; 604/5; 604/28; 604/30
[58] Field of Search ........................ 604/4–6, 604/19, 27, 28, 29, 30; 210/87, 646

[56] References Cited

U.S. PATENT DOCUMENTS

| | | | |
|---|---|---|---|
| 4,650,457 | 3/1987 | Morioka et al. | 604/4 |
| 4,776,837 | 10/1988 | Ropp | 604/4 |
| 4,828,543 | 5/1989 | Weiss et al. | 604/4 |
| 4,885,001 | 12/1989 | Leppert | 604/4 |
| 4,940,455 | 7/1990 | Guinn | 604/5 |
| 5,092,836 | 3/1992 | Polaschegg | 604/4 |
| 5,098,373 | 3/1992 | Polaschegg | 604/5 |

FOREIGN PATENT DOCUMENTS 2417900  4/1973  Fed. Rep. of Germany .......... 604/4

Primary Examiner—Robert A. Hafer
Assistant Examiner—Sam Rimell
Attorney, Agent, or Firm—Finnegan, Henderson, Farabow, Garrett & Dunner

[57] ABSTRACT

A single needle extracorporeal blood circuit for connection to a blood treatment device includes an arterial portion having an arterial reservoir, an end for connection to the needle, an end for connection to the blood treatment device, and a first valve for flow communicating the needle with the arterial reservoir. The blood circuit also includes a venous portion having a venous reservoir, an end for connection to the blood treatment device, an end for connection to the needle, and a second valve for flow communicating the needle with the venous reservoir. Detectors monitor quantities of liquid in the arterial and venous reservoirs so that the first valve is opened in response to the presence of a first predetermined quantity of liquid in the arterial reservoir or a second predetermined quantity of liquid in the venous reservoir. Similarly, the second valve is opened in response to the presence of either a third predetermined quantity of liquid in the arterial reservoir or a fourth predetermined quantity of liquid in the venous reservoir.

28 Claims, 2 Drawing Sheets

METHOD AND APPARATUS FOR CONTROLLING THE CIRCULATION OF BLOOD IN A SINGLE NEEDLE CIRCUIT

BACKGROUND OF THE INVENTION

1. Field of the Invention

The present invention relates to the field of extracorporeal blood circulation in a single needle circuit. More particularly, the invention relates to a method and apparatus for controlling alternating flow within a single needle circuit having arterial and venous stages.

2. Description of the Related Art

In an extracorporeal treatment, blood is drawn from the patient, treated by an appropriate device and then restored to the patient. The drawing and restoration of blood to the patient can be undertaken via two different access points on the patient's body. However, when treatments have to be carried out in a repetitive manner such as is necessary with dialysis treatments of patients with chronic renal insufficiencies, it is advantageous to limit the number of punctures and to use a single needle extracorporeal blood circuit. In a single needle circuit, blood is drawn and restored to the patient via a single vascular access point. When a single needle system is used, the blood must alternately circulate from the needle in one direction and then to the needle in an opposite direction. It is therefore necessary to resolve problems associated with the alternation of the aspiration or arterial stages and the restoration or venous stages.

U.S. Pat. No. 4,776,837 relates to a single needle extracorporeal circuit, including an arterial portion comprising an arterial reservoir and means for opening and closing of the circuit situated ahead of the arterial reservoir and downstream from the needle. It also includes a venous portion comprising a venous reservoir and means for opening and closing the circuit situated downstream of the venous reservoir and upstream of the needle.

According to U.S. Pat. No. 4,776,837, the operation of the venous stage, also referred to as the blood restoration stage, is initiated in response to the presence of a top quantity limit of liquid inside the venous reservoir. Similarly, the operation of the arterial stage, also referred to as the blood aspiration stage, is initiated in response to the presence of a bottom quantity limit of liquid inside the arterial reservoir.

The authors of the '837 patent suggest that their method for alternately operating the arterial and venous stages is self-regulating and affords an optimum use of treatment time because the arterial stage is only started when the quantity of liquid present in the arterial reservoir becomes insufficient, and the venous stage is only started when an adequate quantity of liquid is present in the venous reservoir.

However, there are safety problems with this related art control method. During the arterial stage, the quantity of liquid increases simultaneously in both the arterial and venous reservoirs. If the upper limit condition is only detected in the venous reservoir, it is possible for an unduly high quantity of liquid to be present in the arterial reservoir before the top quantity limit is reached in the venous reservoir, which can result in blood overflowing from the arterial reservoir.

Similarly, during the venous stage, the quantity of liquid diminishes simultaneously in the two reservoirs. If only the presence of a bottom quantity limit in the arterial reservoir is detected, the quantity of liquid present in the venous reservoir may become insufficient. There is then a risk that air will be injected into the patient along with treated blood, which can cause serious disorders such as embolisms.

SUMMARY OF THE INVENTION

To remedy the drawbacks of the related art, the object of the present invention is to provide a method and apparatus for controlling the alternation of blood aspiration and restoration stages in a single needle extracorporeal circuit constituted by an arterial portion comprising an arterial reservoir, as well as means for the opening and closing of the circuit situated ahead of the said reservoir and a venous portion. The venous portion includes a venous reservoir as well as means for opening and closing of the circuit situated downstream of the reservoir. According to the invention, the aspiration stage is begun as soon as a specified minimum quantity of liquid has been reached in either the arterial or venous reservoirs. Similarly, the restoration stage is begun as soon as a specified maximum quantity of liquid has been reached in one or the other of the reservoirs.

According to a particular embodiment of the invention, there is provided means for registering the presence of a specified maximum quantity of liquid in the reservoirs by detecting that a high liquid level has been reached in the reservoirs. There is also provided means for registering the presence of a specified minimum quantity of liquid in the reservoirs by detecting that a low liquid level has been reached in the reservoirs.

Thus, the quantities of liquid inside the chambers are controlled directly without any need for correlating, for example, the quantity of liquid present in a chamber with the pressure in the chamber.

Moreover, the risk of spillovers from the reservoir and the risk of introducing air into the circulating blood are completely avoided. Furthermore, the control process is particularly suited to devices wherein the arterial and venous pressures are kept substantially constant.

According to a particularly advantageous mode of embodiment, a method of the invention includes the step of checking that the specified maximum quantity of liquid is obtained simultaneously in the two reservoirs, and that the specified minimum quantity of liquid is obtained simultaneously in the two reservoirs.

This makes it possible to maintain complete control of the volume of blood available for treatment and to optimize the efficiency of the treatment for a given period.

The description refers to an extracorporeal blood treatment in connection with a dialysis and/or ultrafiltration apparatus. However, the present invention is not limited in scope to such use since both the method and apparatus of the invention can be used for any extracorporeal circulation of the blood in a single needle circuit.

Additional objects and advantages of the invention will be set forth in part in the description that follows, and in part will be obvious from the description or maybe learned by practice of the invention. The objects and advantages of the invention will be realized and attained by means of the elements and combinations particularly pointed out in the appended claims.

It is to be understood that both the foregoing general description and the following detailed description are exemplary and explanatory only, and are not restrictive of the invention, as claimed.

BRIEF DESCRIPTION OF THE DRAWINGS

The accompanying drawings, which are incorporated in and constitute a part of the specification, illustrate several embodiments of the invention, and together with the description, serve to explain the principles of the invention.

DESCRIPTION OF THE PREFERRED EMBODIMENTS

Reference will now be made in detail to the present preferred embodiments of the invention. Wherever possible, the same reference number will be used throughout the description and drawings to refer to the same or like parts.

Figure 1:
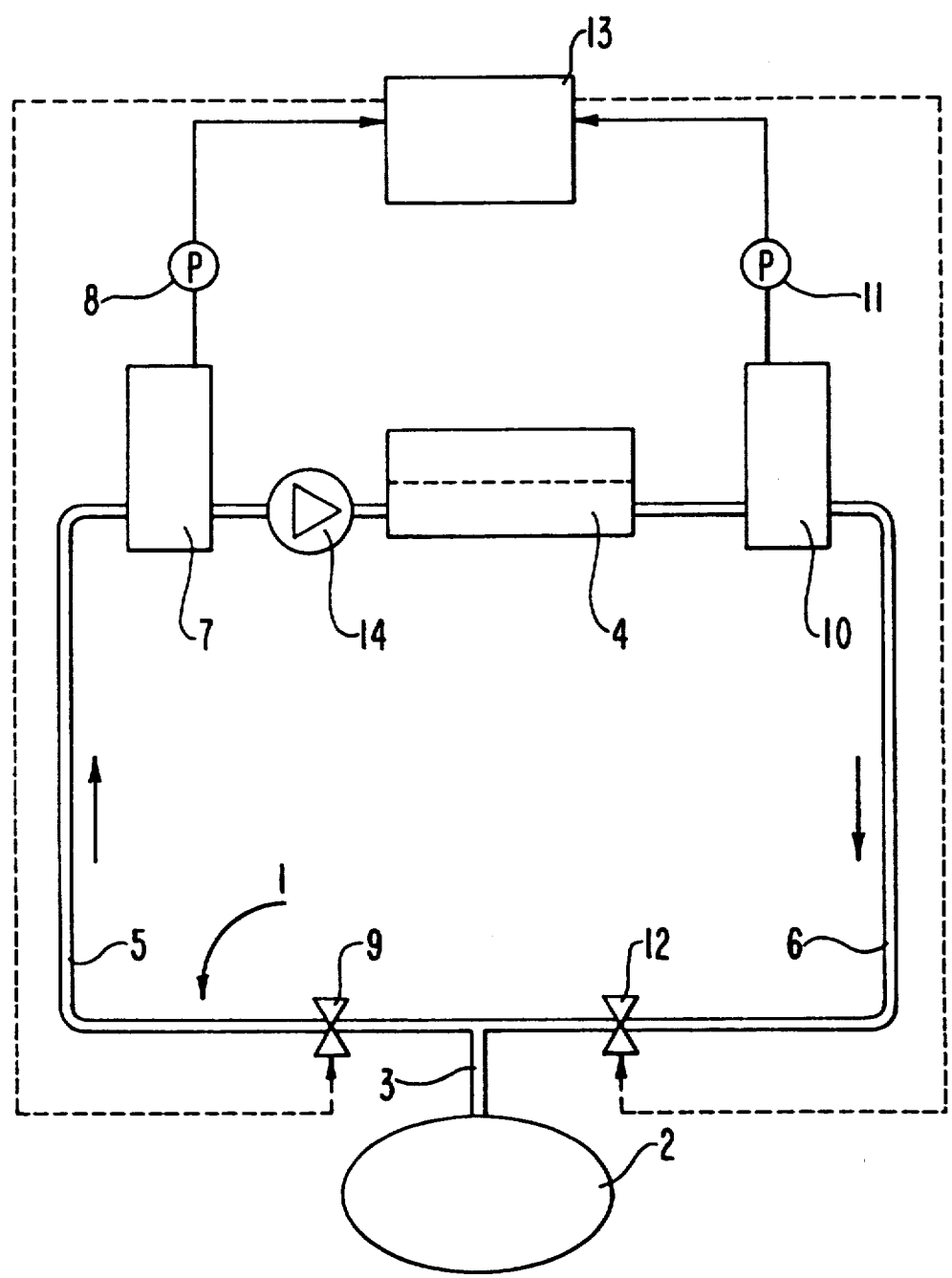
FIG. 1 is a schematic diagram of a first embodiment of the apparatus of the present invention.

As shown in FIG. 1, the extracorporeal circuit 1 allows blood to be drawn from a patient 2 via a single access such as needle 3. The blood circulates through extracorporeal circuit 1 and is restored to the patient through single needle access 3 after treatment by a device such as a haemodialyser 4. The extracorporeal circuit 1 includes an arterial portion 5 for circulating the blood to be treated between the needle 3 and the haemodialyser 4. Circuit 1 also includes a venous portion 6 for circulating the treated blood between the haemodialyser 4 and the needle 3.

The arterial portion 5 includes an arterial reservoir 7 provided with a pressure transducer 8 as well as means for opening and closing the circuit, such as clamp 9. Similarly, the venous portion 6 includes a venous reservoir 10 provided with a pressure transducer 11 as well as means for opening and closing the circuit, such as clamp 12. Data coming from the pressure transducers 8 and 11 are transmitted to a control unit 13, which controls the opening and closing of clamps 9 and 12.

A pump 14 is situated in the arterial portion 5 between the reservoir 7 and the haemodialyser 4.

The single needle extracorporeal circuit operates in the conventional way by alternating the arterial stages and the venous stages. During the arterial stage, the clamp 9 is open and the clamp 12 is closed. Blood is drawn from the patient and is circulated from the needle 3 through the arterial portion 5, the haemodialyser 4 and the venous portion 6 due to the action of the pump 14. Since the clamp 12 is closed, the quantity of liquid inside the reservoirs 7 and 10 increases. In addition, since the reservoirs are closed, the internal reservoir pressure also increases as the volume of liquid increases.

On the other hand, during the venous stage, the clamp 12 is open, the clamp 9 is closed, and the blood is restored to the patient. Blood circulation through the haemodialyser 4 is maintained, due to the liquid present in the reservoir 7. As the quantity of liquid inside the reservoirs 7 and 10 diminishes, their internal pressures are also reduced.

The pressure inside the arterial portion 5 is always negative and varies between approximately $-200$ mmHg ($-2.67 \cdot 10^4$Pa in relation to atmospheric pressure) at the end of the arterial stage, and $-350$ mmHg ($-4.6 \cdot 10^4$Pa in relation to atmospheric pressure) at the end of the venous stage. The pressure inside the venous portion is a positive pressure which varies between approximately $+200$ mmHg ($2.67 \cdot 10^4$Pa) at the end of the venous stage, and $+350$ mmHg ($4.6 \cdot 10^4$Pa) at the end of the arterial stage.

The pressures inside the chambers are set at the start of a treatment session. The maximum and minimum pressure values are chosen according to the known geometry of the extracorporeal circuit and in particular, according to the volume of the reservoirs 7 and 10. These volumes correspond to the specified maximum and minimum quantities and hence to a specified variation of the quantity of liquid inside each reservoir between the arterial stage and the venous stage. Moreover, the pressure values are chosen in order to be haemocompatible and to correspond to appropriate levels of liquid inside the reservoirs.

According to the invention, the measurements taken by the pressure transducers 8 and 11 are transmitted to the control unit 13 which compares them with the values stored in the memory during the initial setting, for example, $-350$ mmHg and $-200$ mmHg for the arterial pressure values measured by the transducer 8, and $+200$ mmHg and $+350$ mmHg for the venous pressure values measured by the transducer 11.

Thus, when the device is in the arterial stage and when the quantity of liquid increases in the reservoirs, as soon as the measured pressure reaches $-200$ mmHg in the arterial reservoir 7, or $+350$ mmHg in the venous reservoir 10, the unit 13 actuates the closing of the clamp 9 and the opening of the clamp 12. The venous stage then begins, and the quantity of liquid diminishes inside the reservoirs. As soon as the measured pressure reaches $-350$ mmHg in the arterial, or $+200$ mmHg in the venous reservoir, the control unit 13 switches the system to the arterial stage by closing clamp 12 and opening clamp 9.

The above-described apparatus and method of controlling the alternation of the arterial and venous stages of extracorporeal circuit 1 represents a marked safety improvement as compared with the related art device described earlier.

Figure 2:
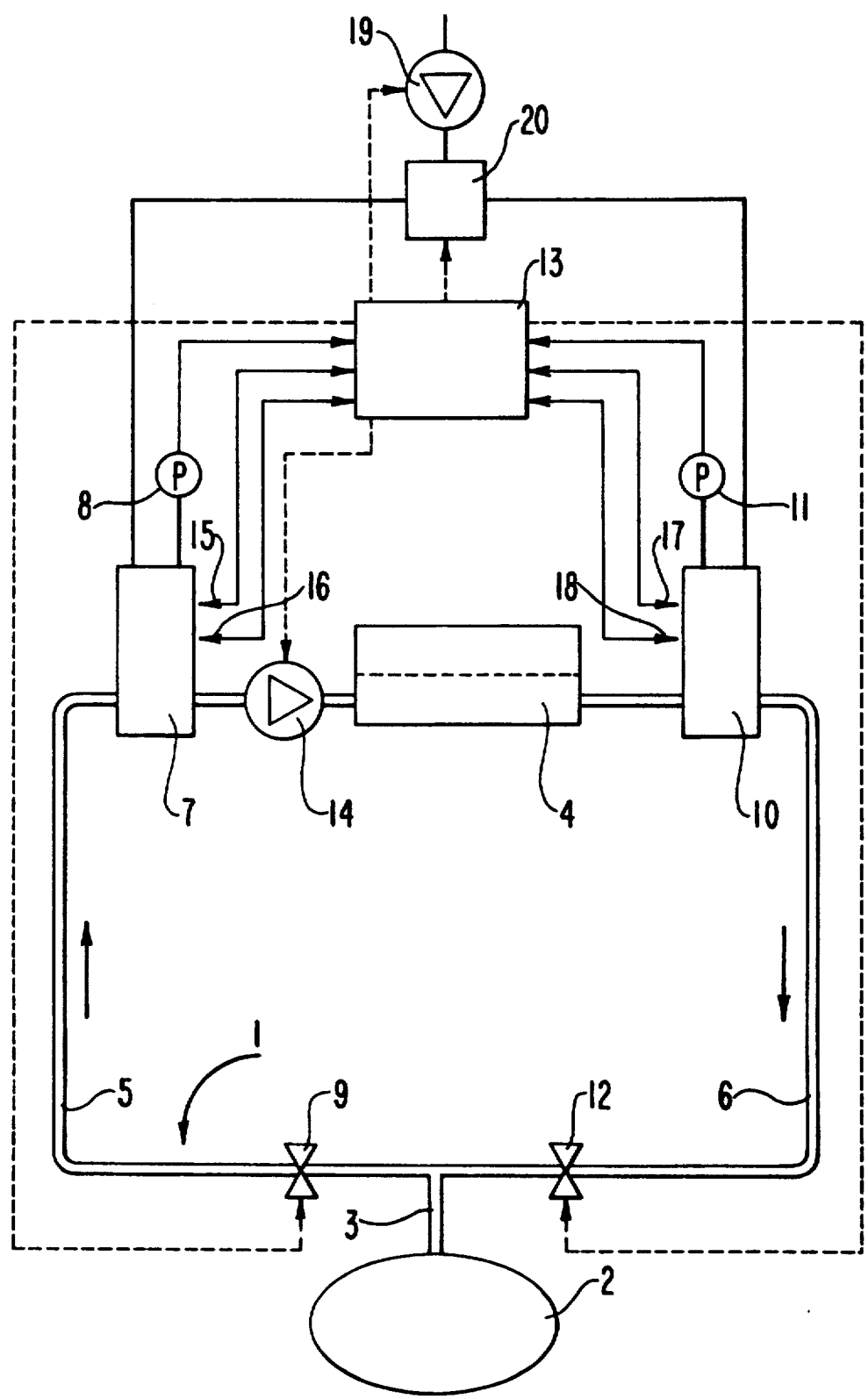
FIG. 2 is a schematic diagram of a second embodiment of the apparatus of the present invention.

FIG. 2 illustrates second embodiment of the present invention. The elements in FIG. 2 that are substantially identical to those of FIG. 1 bear the same reference numerals. According to this embodiment, the arterial reservoir 7 and venous reservoir 10 are each provided with two level detectors whose positions correspond to the desired maximum and minimum quantities of liquid inside the reservoirs. Thus, the arterial reservoir 7 is provided with a high level detector 15 and a low level detector 16. Similarly, the venous reservoir 10 is provided with a high level detector 17 and a low level detector 18.

Data from level detectors 15, 16, 17 and 18 are transmitted to control unit 13. The circuit also includes a gas pump 19 that can, depending upon the position of a distributor 20, selectively pump a gas, such as air to the arterial reservoir 7 or the venous reservoir 10. Pump 19 is controlled by the control unit 13 for permitting gas to be added to, or withdrawn from the reservoirs. A distributor 20, whose position is also controlled by control unit 13, allows pump 19 to communicate selectively with reservoir 7 or reservoir 10.

According to this embodiment, when, at the end of the arterial stage, the liquid reaches the specified maximum quantity in either of the reservoirs, a corresponding high level detector (15, 17) emits a signal which is transmitted to the control unit 13. The control unit 13 then ensures the operation of the venous stage by opening clamp 12 and closing clamp 9. Similarly, at the end of the venous stage, when one of the low level detectors 16 or 18 is reached, the control unit 13 starts the operation of the arterial stage by actuating the opening of clamp 9 and the closing clamp 12.

Thus the changeover from one stage to the other is not only effected in accordance with what is occurring in only one portion of the circuit without considering what is simultaneously happening in the other, but it is, on the contrary, regulated in accordance with the operating conditions of the circuit as a whole. Moreover, under certain conditions there may be certain simplicity and reliability benefits to using liquid level detectors instead of pressure transducers.

To optimize the efficiency of blood treatment in the extracorporeal circuit, the method of the invention also makes it possible to check that the liquid level in each reservoir really does vary between the high level and the low level. Indeed, at the end of the arterial stage, when the control unit 13 is informed that the liquid has reached the high level detector in a first reservoir, it starts a time measurement in the other reservoir, in order to measure the amount of time that the liquid takes to reach the low level detector in the second reservoir. This period of time is then compared by the control unit 13 with a reference period which is determined from the known volume existing between the high level detector and the low level detector and the operating conditions of the circuit such as the delivery characteristics of the pump 14 and the pressure values set at the start of the session. This reference period corresponds to the time which the liquid level should take to fall if it had reached the high level at the same time as the liquid in the first reservoir. The difference between the measured period and the reference period makes it possible to assess the level at which the liquid was situated in the second reservoir at the moment when the liquid reached the high level detector in the first reservoir.

If the measured period does no correspond to the reference period or is at least not in a reference range, then the pressure conditions inside at least one reservoir is not at a desired level. Using measurements taken by the transducers 8 and 11, the control unit 13 can determine in which reservoir the discrepancy has taken place. A correction can then be effected by adding or withdrawing air by means of the pump 19. The effectiveness of the correction can be checked by taking another measurement during the following cycle. It is, of course, possible to start the time measurement in a similar manner when, at the end of the venous stage, the liquid level reaches the low level detector in one reservoir. In this situation, the time the liquid takes to rise in the other reservoir is measured.

According to the invention, it is also possible to vary the volume of blood available for treatment by varying the location of the level detectors.

The present invention is not limited to the examples described but is amenable to many variants. Instead of using two "all or nothing" level detectors for each reservoir, it is possible to use only a single detector for transmitting a signal that is directly proportional to the liquid level in the reservoir. Thus, for checking that the liquid reaches the high level and the low level in each reservoir simultaneously, it suffices, when a limiting level (high or low) has been reached in one reservoir, for the control unit 13 to check that the signal transmitted by the level detector in the other reservoir is also within a reference range. Otherwise, the control unit 13 actuates the operation of the pump 19 and the distributor 20 in order to reestablish the desired operating conditions.

What is claimed is:

1. A single needle extracorporeal blood circuit for connection to a blood treatment device, the blood circuit comprising:
    an arterial portion having a first end for connection to the needle and a second end for connection to the blood treatment device, the arterial portion including an arterial reservoir;
    a venous portion having a first end for connection to the blood treatment device and a second end for connection to the needle, the venous portion including a venous reservoir;
    valve means actuate between a first position for flow communicating the needle with the arterial reservoir, and a second position for flow communicating the needle with the venous reservoir;
    means for monitoring quantities of liquid in the arterial reservoir and in the venous reservoir; and
    a controller including first means for actuating the valve means to the first position in response to detection by the monitoring means of a first predetermined quantity of liquid in the arterial reservoir and for actuating the valve means to the first position in response to detection of a second predetermined quantity of liquid in the venous reservoir, and second means for actuating the valve means to the second position in response to detection by the monitoring means of a third predetermined quantity of liquid in the arterial reservoir and for actuating the valve means to the second position in response to detection of a fourth predetermined quantity of liquid in the venous reservoir.

2. A single needle extracorporeal blood circuit as set forth in claim 1 wherein the first and second predetermined quantities are predetermined minimum quantities for the respective arterial and venous reservoirs, and the third and fourth quantities are predetermined maximum quantities for the respective arterial and venous reservoirs.

3. A single needle extracorporeal blood circuit as set forth in claim 1 wherein the monitoring means includes pressure sensing means for determining the quantity of liquid in each of the arterial and venous reservoirs based upon the pressure in the reservoirs.

4. A single needle extracorporeal blood circuit as set forth in claim 3 wherein the pressure sensing means includes a first pressure detector connected to the arterial reservoir and a second pressure detector connected to the venous reservoir.

5. A single needle extracorporeal blood circuit as set forth in claim 1 wherein the monitoring means includes a high level detector and a low level detector associated with each of the arterial and venous reservoirs.

6. A single needle extracorporeal blood circuit as set forth in claim 1 further including pump means for moving liquid through the circuit.

7. A single needle extracorporeal blood circuit as set forth in claim 1 further including means for introducing a gas into the arterial and venous reservoirs.

8. A single needle extracorporeal blood circuit as set forth in claim 7 wherein the gas introducing means includes a pump.

9. A single needle extracorporeal blood circuit as set forth in claim 8 wherein the gas introducing means also includes a distributor for selectively flow communicating the pump with the arterial and venous reservoirs.

10. A single needle extracorporeal blood circuit as set forth in claim 1 wherein the valve means includes a first valve and a second valve, the first valve being disposed in the arterial portion and the second valve being disposed in the venous portion.

11. A method for controlling a single needle extracorporeal blood circuit for attachment to a blood treatment device, the method comprising the steps of:
monitoring a blood quantity in an arterial reservoir disposed in the blood circuit;
monitoring a blood quantity in a venous reservoir disposed in the blood circuit;
initiating blood flow from a patient to the arterial reservoir when a first predetermined quantity of blood is detected in the arterial reservoir;
initiating blood flow from a patient to the arterial reservoir when a second predetermined quantity of blood is detected in the venous reservoir;
initiating blood flow from the venous reservoir to the patient when a third predetermined quantity of blood is detected in the arterial reservoir; and
initiating blood flow from the venous reservoir to the patient when a fourth predetermined quantity of blood is detected in the venous reservoir.

12. A method for controlling a single needle extracorporeal blood circuit as set forth in claim 11 wherein the first and second predetermined quantities are predetermined minimum quantities for the respective arterial and venous reservoirs, and the third and fourth quantities are predetermined maximum quantities for the respective arterial and venous reservoirs.

13. A method for controlling a single needle extracorporeal blood circuit as set forth in claim 12 further including the step of determining the quantity of liquid in the venous reservoir when the first predetermined quantity is detected in the arterial reservoir, and modifying the quantity of gas in at least one of said arterial and venous reservoirs if the determined quantity of liquid in the venous reservoir is not substantially equal to the second predetermined quantity.

14. A method for controlling a single needle extracorporeal blood circuit as set forth in claim 12 further including the step of adding a quantity of gas to either of the arterial or venous reservoirs if the maximum predetermined liquid quantity is attained in one of the reservoirs before the maximum predetermined liquid quantity is attained in the other of said reservoirs.

15. A method for controlling a single needle extracorporeal blood circuit as set forth in claim 12 further including the step of withdrawing a quantity of gas from either of the arterial or venous reservoirs if the maximum predetermined liquid quantity is attained in one of the reservoirs before the maximum predetermined liquid quantity is attained in the other of said reservoirs.

16. A method for controlling a single needle extracorporeal blood circuit as set forth in claim 13 wherein the gas is air.

17. A method for controlling a single needle extracorporeal blood circuit as set forth in claim 12 further including the step of adding a quantity of gas to either of the arterial or venous reservoirs if the minimum predetermined quantity is attained in one of the reservoirs before the minimum predetermined quantity is attained in the other of said reservoirs.

18. A method for controlling a single needle extracorporeal blood circuit as set forth in claim 12 further including the step of withdrawing a quantity of as from either of the arterial or venous reservoirs if the minimum predetermined quantity is attained in one of the reservoirs before the minimum predetermined quantity is attained in the other of said reservoirs.

19. A method for controlling a single needle extracorporeal blood circuit as set forth in claim 14 wherein the gas is air.

20. A method for controlling a single needle extracorporeal blood circuit as set forth in claim 11 wherein the step of monitoring the blood level in the reservoirs includes the substep of determining the pressures in each of the reservoirs.

21. A method for controlling a single needle extracorporeal blood circuit as set forth in claim 12 further including the step of determining the quantity of liquid in the arterial reservoir when the second predetermined quantity is detected in the venous reservoir, and modifying the quantity of gas in at least one of said arterial and venous reservoirs if the determined quantity of liquid in the arterial reservoir is not substantially equal to the first predetermined quantity.

22. A method for controlling a single needle extracorporeal blood circuit as set forth in claim 12 further including the step of determining the quantity of liquid in the venous reservoir when the third predetermined quantity is detected in the arterial reservoir, and modifying the quantity of gas in at least one of said arterial and venous reservoirs if the determined quantity of liquid in the venous reservoir is not substantially equal to the fourth predetermined quantity.

23. A method for controlling a single needle extracorporeal blood circuit as set forth in claim 12 further including the step of determining the quantity of liquid in the arterial reservoir when the fourth predetermined quantity is detected in the venous reservoir, and modifying the quantity of gas in at least one of said arterial and venous reservoirs if the determined quantity of liquid in the arterial reservoir is not substantially equal to the third predetermined quantity.

24. A method for controlling a single needle extracorporeal blood circuit for attachment to a blood treatment device, the method comprising the steps of:
(a) monitoring the blood level in a arterial reservoir disposed in the blood circuit;
(b) monitoring the blood level in a venous reservoir disposed in the blood circuit;
(c) initiating blood flow from a patient to the arterial reservoir when a first predetermined quantity of blood is detected in the arterial reservoir;
(d) initiating blood flow from a patient to the arterial reservoir when a second predetermined quantity of blood is detected in the venous reservoir;
(e) initiating blood flow for the venous reservoir to the patient when a third predetermined quantity of blood is detected in the arterial reservoir;
(f) initiating blood flow from the venous reservoir to the patient when a fourth predetermined quantity of blood is detected in the venous reservoir;
(g) varying an amount of gas in at least one of the arterial and venous reservoirs if one of the first and second predetermined quantities is reached before the other of said first and second predetermined quantities is reached; and
(h) varying an amount of gas in at least one of the arterial and venous reservoirs if one of the third and fourth predetermined quantities is reached before the other of said third and fourth predetermined quantities is reached.

25. A method as set forth in claim 24 wherein step (g) sequentially follows at least one of steps (c) and (d), and step (h) sequentially follows at least one of steps (e) and (f).

26. A method as set forth in claim 24 wherein the gas is varied in step (g) in order for the other of said first and second predetermined quantities to be reached.

27. A method as set forth in claim 24 wherein the gas is varied in step (h) in order for the other of said third and fourth predetermined quantities to be reached.

28. A single needle extracorporeal blood circuit as set forth in claim 1 wherein the monitoring means includes level detector means for determining quantities of liquid in each of the arterial and venous reservoirs.

* * * * *

UNITED STATES PATENT AND TRADEMARK OFFICE
CERTIFICATE OF CORRECTION

PATENT NO.   : 5,318,511

DATED        : June 7, 1994

INVENTOR(S)  : Jean-Claude Riquier and Jacques Chevallet

Page 1 of 2

It is certified that error appears in the above-indentified patent and that said Letters Patent is hereby corrected as shown below:

Claim 1, column 6, line 15, replace "actuate" with --actuable--.

Claim 11, column 7, lines 9-24, delete in their entirety and insert therefor:

--monitoring a predetermined non-minimum quantity and a predetermined non-maximum quantity of blood in an arterial reservoir disposed in the blood circuit;
simultaneously monitoring a predetermined non-minimum quantity and a predetermined non-maximum quantity of blood in a venous reservoir disposed in the blood circuit;
initiating blood flow from a patient to the arterial reservoir when either a first non-maximum predetermined quantity of blood is detected in the arterial reservoir or a second non-maximum predetermined quantity of blood is detected in the venous reservoir; and
initiating blood flow from the venous reservoir to the patient when either a third non-minimum predetermined quantity of blood is detected in the arterial reservoir or a fourth non-minimum predetermined quantity of blood is detected in the venous reservoir.--

UNITED STATES PATENT AND TRADEMARK OFFICE
CERTIFICATE OF CORRECTION

PATENT NO. : 5,318,511
DATED : June 7, 1994
INVENTOR(S) : Jean-Claude Riquier and Jacques Chevallet It is certified that error appears in the above-indentified patent and that said Letters Patent is hereby corrected as shown below:

Claim 24, column 8, lines 43-64, delete in their entirety and insert therefor:

--(a) monitoring a non-minimum and a non-maximum blood level in an arterial reservoir disposed in the blood circuit;
  (b) simultaneously monitoring a non-minimum and a non-maximum blood level in a venous reservoir disposed in the blood circuit;
  (c) initiating blood flow from a patient to the arterial reservoir when either a first non-maximum predetermined quantity of blood is detected in the arterial reservoir or a second non-maximum predetermined quantity of blood is detected in the venous reservoir;
  (d) initiating blood flow from the venous reservoir to the patient when either a third non-minimum predetermined quantity of blood is detected in the arterial reservoir or a fourth non-minimum predetermined quantity of blood is detected in the venous reservoir;
  (e) varying an amount of gas in at least one of the arterial and venous reservoirs if one of the first and second predetermined quantitites is reached before the other of said first and second predetermined quantities is reached; and
  (f) varying an amount of gas in at least one of the--.

Signed and Sealed this

Twenty-ninth Day of November, 1994

Attest:

BRUCE LEHMAN

Attesting Officer            Commissioner of Patents and Trademarks